(12) United States Patent
Canepa et al.

(10) Patent No.: US 12,714,577 B2
(45) Date of Patent: Aug. 25, 2026

(54) HIP STEM ALIGNMENT GUIDE

(71) Applicant: Howmedica Osteonics Corp., Mahwah, NJ (US)

(72) Inventors: Polina Canepa, Wyckoff, NJ (US); Katrina David, Sayreville, NJ (US); Christopher Heffernan, Dumont, NJ (US); Rachel Gibbons, Easton, PA (US); Fares Haddad, London (GB); Michael Masini, Ann Arbor, MI (US)

(73) Assignee: Howmedica Osteonics Corp., Mahwah, NJ (US)

( * ) Notice: Subject to any disclaimer, the term of this patent is extended or adjusted under 35 U.S.C. 154(b) by 836 days.

(21) Appl. No.: 18/173,139

(22) Filed: Feb. 23, 2023

(65) Prior Publication Data

US 2023/0277334 A1 Sep. 7, 2023

Related U.S. Application Data

(60) Provisional application No. 63/315,587, filed on Mar. 2, 2022.

(51) Int. Cl.
*A61F 2/46* (2006.01)
*A61F 2/36* (2006.01)

(52) U.S. Cl.
CPC .......... *A61F 2/4607* (2013.01); *A61F 2/3609* (2013.01); *A61F 2/4684* (2013.01); (Continued)

(58) Field of Classification Search
CPC ............ A61F 2002/4687; A61F 2/4607; A61F 2/4684; A61F 2/3609; A61F 2002/3652; (Continued)

(56) References Cited

U.S. PATENT DOCUMENTS 5,342,362 A * 8/1994 Kenyon .................. A61F 2/468 606/85
5,514,136 A * 5/1996 Richelsoph ........... A61F 2/4607 606/86 R (Continued)

FOREIGN PATENT DOCUMENTS

CN 118217062 A * 6/2024 ........... A61F 2/4607
EP 1022001 A1 7/2000
FR 2770128 A1 4/1999

OTHER PUBLICATIONS

Stryker, "Exeter® V40® Femoral Stem using Exeter Broach Surgical technique", (2019). 20 pgs.

*Primary Examiner* — Alvin J Stewart
(74) *Attorney, Agent, or Firm* — Lerner David LLP

(57) ABSTRACT

A prosthesis alignment guide includes a guide body that has an opening that extends at least partially therein and a first alignment hole extending entirely therethrough. The opening is configured to receive a trunnion of a joint prosthesis for mounting the guide body to the joint prosthesis. An alignment member is disposed within the first alignment hole and is axially moveable therein. A locking member is engaged to the guide body and moveable from a first position in which the locking member is disengaged from the alignment member and a second position in which the locking member engages the alignment member and secures it from axial movement within the first alignment hole.

19 Claims, 6 Drawing Sheets

(52) U.S. Cl.
CPC ................. *A61F 2002/3625* (2013.01); *A61F 2002/3652* (2013.01); *A61F 2002/4687* (2013.01)

(58) Field of Classification Search
CPC ......... A61F 2002/3625; A61B 17/8897; A61B 17/90
See application file for complete search history.

(56) References Cited

U.S. PATENT DOCUMENTS

| | | | | | |
|---|---|---|---|---|---|
| 5,593,451 | A | * | 1/1997 | Averill | A61B 17/1668<br>623/23.35 |
| 5,743,910 | A | * | 4/1998 | Bays | A61F 2/4607<br>606/99 |
| 5,792,143 | A | * | 8/1998 | Samuelson | A61F 2/4607<br>606/102 |
| 5,888,245 | A | * | 3/1999 | Meulink | A61F 2/4657<br>606/86 R |
| 6,117,138 | A | * | 9/2000 | Burrows | A61F 2/4684<br>606/86 R |
| 6,165,177 | A | * | 12/2000 | Wilson | A61F 2/4607<br>606/100 |
| 7,828,805 | B2 | | 11/2010 | Hoag et al. | |

* cited by examiner

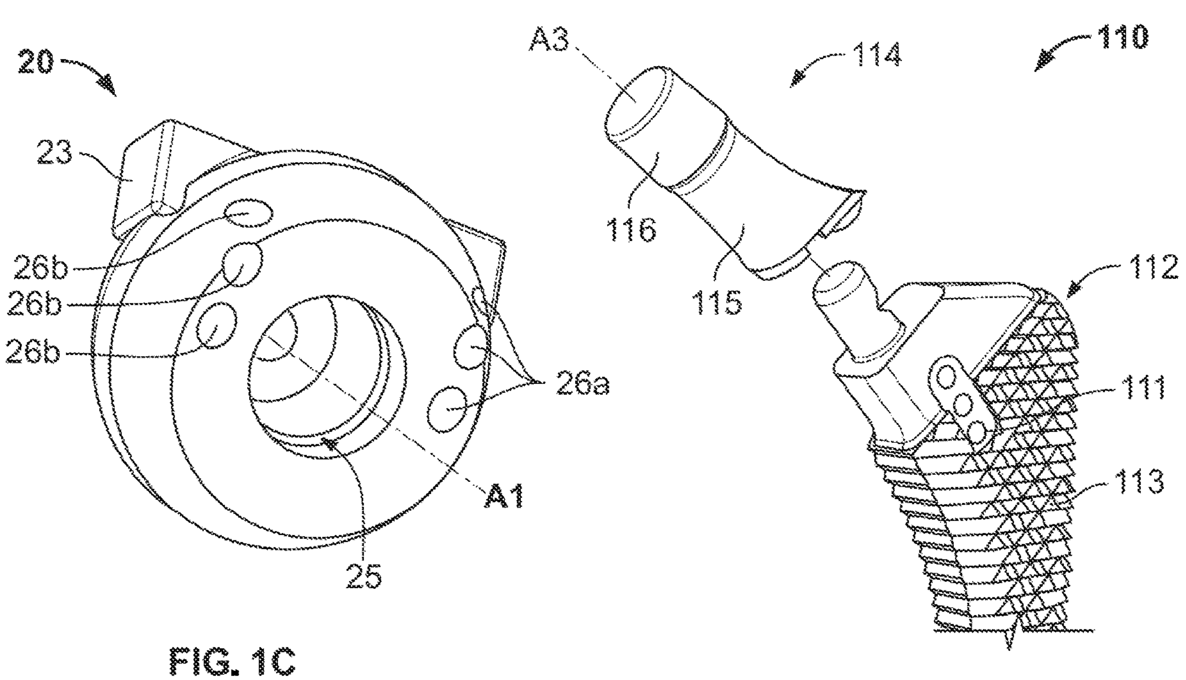
FIG. 1C
FIG. 2A
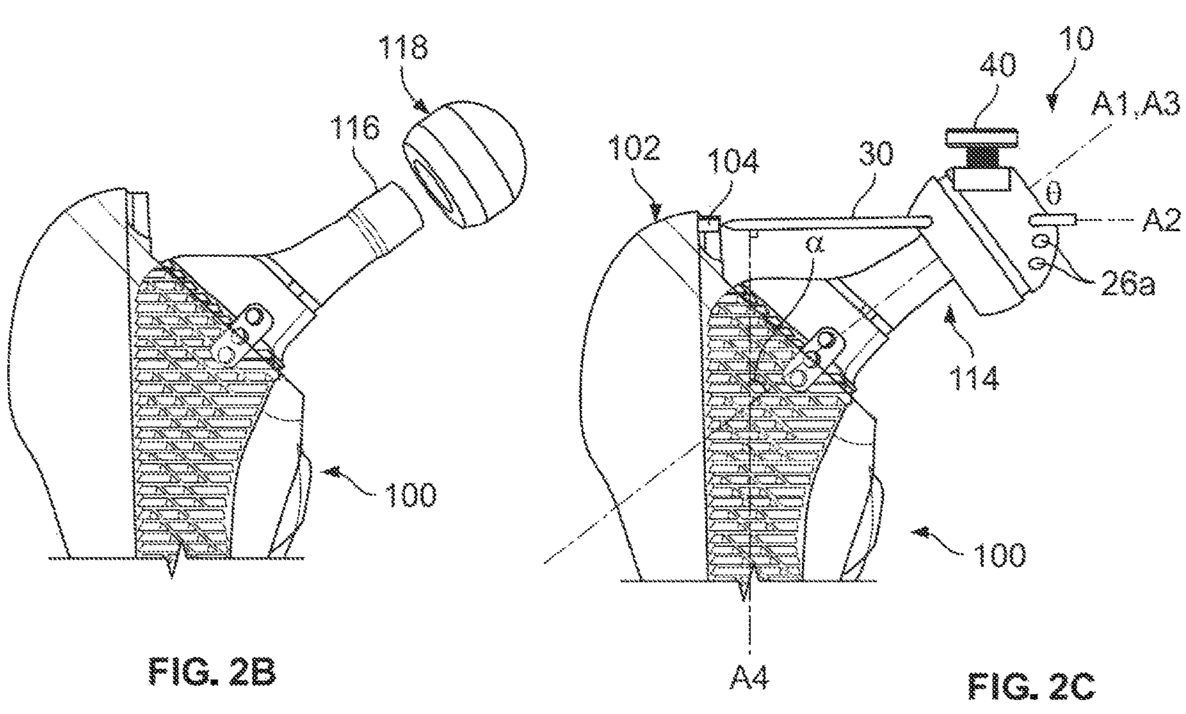
FIG. 2B
FIG. 2C

HIP STEM ALIGNMENT GUIDE

CROSS-REFERENCE TO RELATED APPLICATIONS

This application claims the benefit of the filing date of U.S. Provisional Application No. 63/315,587, filed Mar. 2, 2022, the disclosure of which is hereby incorporated by reference.

BACKGROUND OF THE INVENTION

Joint arthroplasty procedures generally involve the replacement of a damaged or diseased articular surface with an artificial surface of a joint prosthesis. This typically includes resecting the bone that underlies the native articular surface in a manner that shapes the remaining bone to accommodate the joint prosthesis. The joint prosthesis is secured to the underlying bone typically through a press-fit arrangement or with the aid of bone cement. When utilizing bone cement, a cement mantle of sufficient thickness is placed between the bone and prosthesis. Although bone cement is rather viscous, movement between the prosthesis and bone is possible until the mantle has cured. Thus, it is imperative that the surgeon properly places the prosthesis in the desired position and orientation until the cement cures. However, this can be challenging particularly in procedures in which there are few, if any, reliable ways to ensure the prosthesis is in the desired multi-dimensional position prior to the cement mantle curing. Therefore, further improvements are desirable.

BRIEF SUMMARY OF THE INVENTION

The present disclosure describes devices, systems, and methods for aligning a stemmed prosthesis relative to a long bone. In particular, an alignment guide is described as including a guide body, an alignment member, and a locking member. The alignment guide may be provided in a system that includes a femoral prosthesis trial and a femoral prosthesis. In operation, an operator may implant the femoral prosthesis trial in a femur to determine a desired position and orientation for the femoral prosthesis. The alignment guide may be mounted to the femoral trial prosthesis, and the alignment member may be secured in a fixed position relative to the guide body via the locking member. The bone may be marked at a location aligned with the alignment member of the alignment guide. The femoral trial prosthesis may be removed from the femur, and the alignment guide may be mounted to the femoral prosthesis. Bone cement may be introduced into the intramedullary canal of the femur. The femoral prosthesis, with the alignment guide mounted thereto, may be inserted into the intramedullary canal. The femoral prosthesis and alignment guide may be adjusted together in height, *varus*/valgus, and version until the alignment member is aligned with a target location on the bone. The bone cement may be allowed to cure while the femoral prosthesis is in the aligned position and orientation. The alignment guide may then be removed, and the surgical procedure may continue.

BRIEF DESCRIPTION OF THE DRAWINGS

The features, aspects, and advantages of the present invention will become better understood with regard to the following description, appended claims, and accompanying drawings in which:

FIG. 1C is a perspective view of a body of the alignment guide of FIG. 1A.

FIG. 2A is a perspective view of a femoral trial assembly according to an embodiment of the present disclosure.

FIG. 2B illustrates the femoral trial assembly of FIG. 2A inserted into a femur and including a femoral head trial according to an embodiment of the present disclosure.

FIG. 2C illustrates the femoral trial assembly of FIG. 2A inserted into a femur and including the alignment guide of FIG. 1 mounted to the femoral trial assembly.

DETAILED DESCRIPTION

Figure 1A:
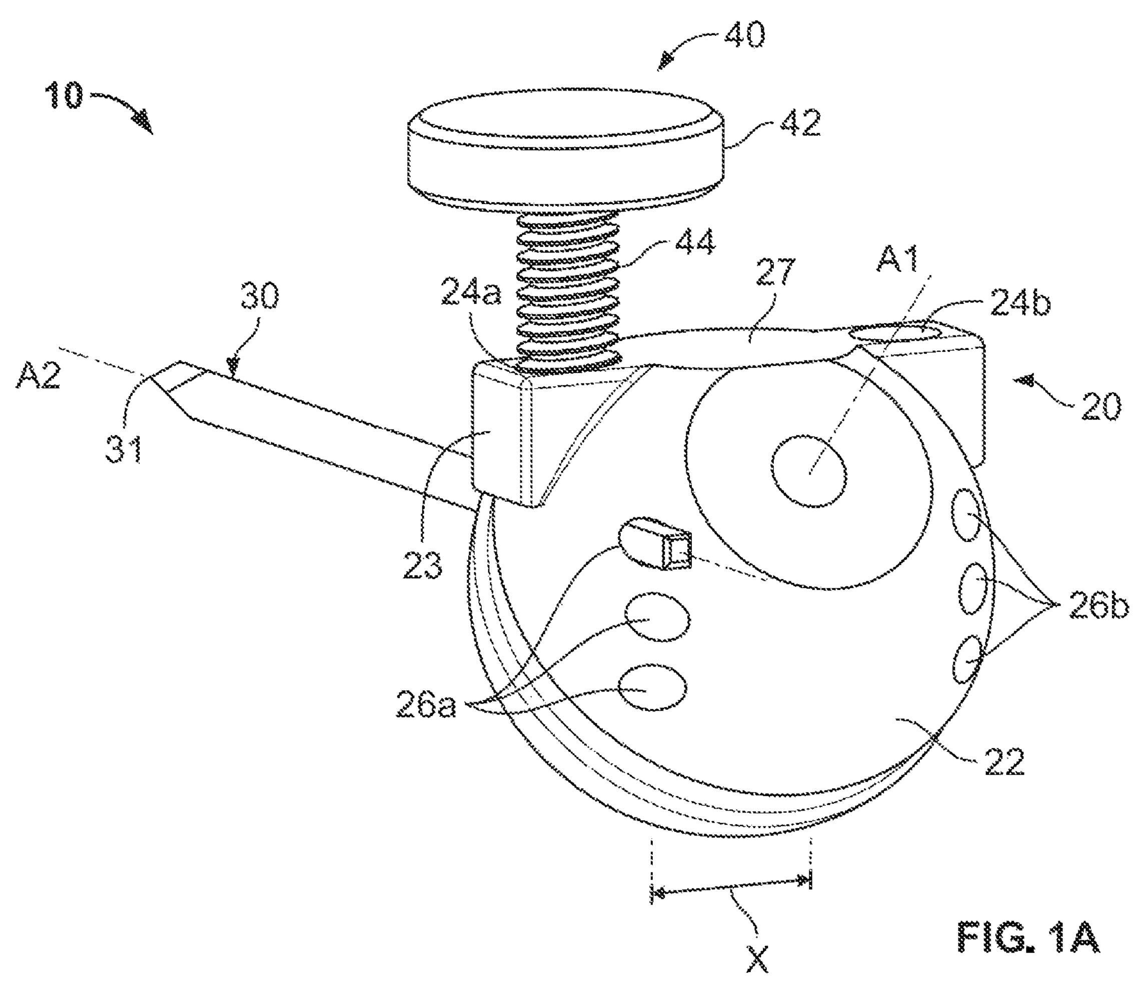
FIG. 1A is a perspective view of an alignment guide according to an embodiment of the present disclosure.
Figure 1B:
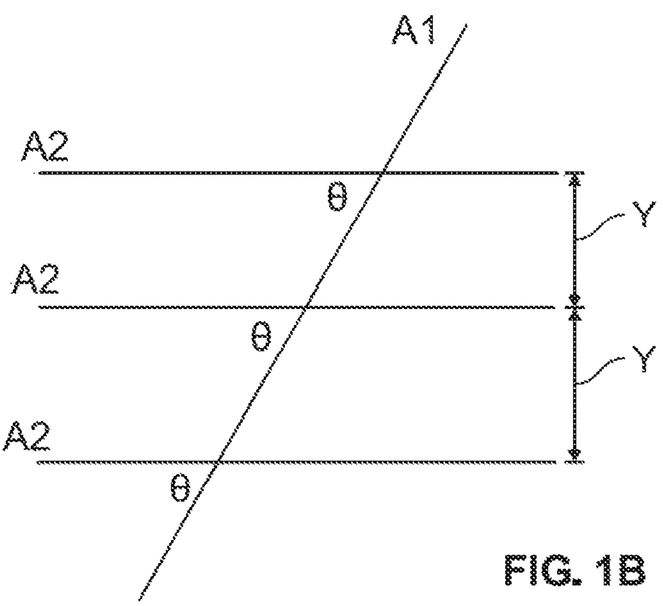
FIG. 1B is a schematic illustrating projected axes of the alignment guide of FIG. 1A.

FIGS. 1A-1C depict an alignment guide 10 according to an embodiment of the present disclosure. Alignment guide 10 generally includes a body 20, an alignment member 30, and a locking member 40.

Guide body 20 includes a spherical portion 22 and a block portion 23. Spherical portion 22 is shaped and sized so that it generally mimics a prosthetic femoral head of a femoral prosthesis, such as the trial femoral head 118 of FIG. 2B, for example. Spherical portion 22 includes a tapered opening configured to receive a tapered trunnion of a femoral prosthesis, as explained further below. Such tapered opening 25, as shown in FIG. 1C, defines a first axis A1 which intersects a geometric center of spherical portion 22. However, it should be understood that first axis A1 may be offset from the geometric center of spherical portion 22 in other embodiments, provided that the offset matches an offset of a final femoral head prosthesis. The spherical shape of spherical portion 22 is generally not intended for articulation with an acetabular cup. Although, in some embodiments it could be used for trial articulation provided block portion 23 is not included in body 20. In this regard, spherical portion 22 can take on other shapes, such as a cube, for example. However, the spherical shape of body 20 is preferable as it helps the surgeon visualize the final construction.

A plurality of alignment holes or through-holes 26*a*-*b* extend entirely through body 20 in an offset relationship relative to first axis A1 and are each configured to slidingly receive alignment member 30. In the embodiment depicted, first and second sets of alignment holes 26*a*-*b* are arranged at opposite sides of first axis A1. First set of alignment holes 26*a* includes three alignment holes 26*a* that each define a second axis A2. Alignment holes 26*a* are evenly spaced by a distance Y and vertically arrayed so that second axis A2 of each hole 26*a* lies in a single plane and in parallel to each other, as best shown in FIG. 1B. This plane is offset from first axis A1 by a distance X, as best shown in FIG. 1A. Distance X is preferably larger than half of a maximum diameter of an implant trunnion, such as trunnion 116 of FIG. 2A, but smaller than half of the diameter of spherical portion 22. This helps ensure that through-holes 26*a-b* are fully captured within spherical portion 22. Holes 26*a* are also oriented so that each axis A2 forms an oblique angle relative to first axis A1. In other words, when axis A1 is projected into the same plane as axes A2, an acute angle θ is formed therebetween, as shown in FIG. 1B. In the embodiment depicted, angle θ is 35 degrees, but may differ depending on the orientation of a femoral neck axis. In other words, a femoral neck axis, such as axis A3 of neck 114 (FIG. 2), may be oriented relative to a stem axis, such as axis A4 of stem 112 (FIG. 2), by an angle α. Angle θ may be selected based on angle α, which is explained in more detail below.

The second set of holes 26*b* are configured the same as the first set of holes 26*a* but at the opposite side of axis A1. In this regard, holes 26*b* of the second set are offset from A1 by distance X and lie in the same plane which is itself parallel to the plane of holes 26*a*. The positioning of first and second holes 26*a-b* at opposite sides of axis A1 allows guide 10 to be universally applied to the left and right legs of a patient. In other words, holes 26*a* of the first set may be used for alignment of a femoral prosthesis relative to a femur of a patient's left leg, and holes 26*b* of the second set may be used for alignment of a femoral prosthesis relative to a right leg femur. Having holes on either side of center axis A1 also accommodates various surgical approaches (e.g., postero-lateral, direct anterior, and the like). The distance Y each hole 26*a-b* is spaced from an adjacent hole 26*a-b* determines an implantation depth of a femoral prosthesis, as explained further below. In some embodiments, indicia (not shown) may be associated with each hole 26*a-b* to indicate the desired implantation depth of a femoral prosthesis.

Block portion 23 of guide body extends outwardly from spherical portion 22 and is offset from first axis A1 and is generally oriented perpendicular to holes 26*a-b*. A first opening 24*a* extends through block portion 23 and into spherical portion 22 so that it intersects each of the first set of alignment holes 26*a*. Similarly, a second opening 24*b* extends through block portion 23 and into spherical portion 22 to intersect each of the second set of alignment holes 26*b*. First and second openings 24*a-b* are threaded along at least a portion of their individual lengths such that they are configured to receive a threaded shaft 44 of locking member 40 (described below).

Alignment member 30 in the depicted embodiment is a headless pin that is configured to be slidingly received within each alignment hole. In this regard, pin 30 is substantially cylindrical and has a pointed tip 31 at one of its ends.

Locking member 40 is a thumbscrew with a head 42 and a threaded shaft 44. Locking member 40 is configured to threadedly engage openings 24*a-b* of guide body 20 and secure alignment member 30 to body 20. In this regard, threaded shaft 44 has a length sufficient to extend to each alignment hole 26*a* and 2*b* from their respective threaded opening 24*a* and 24*b*.

Figure 3A:
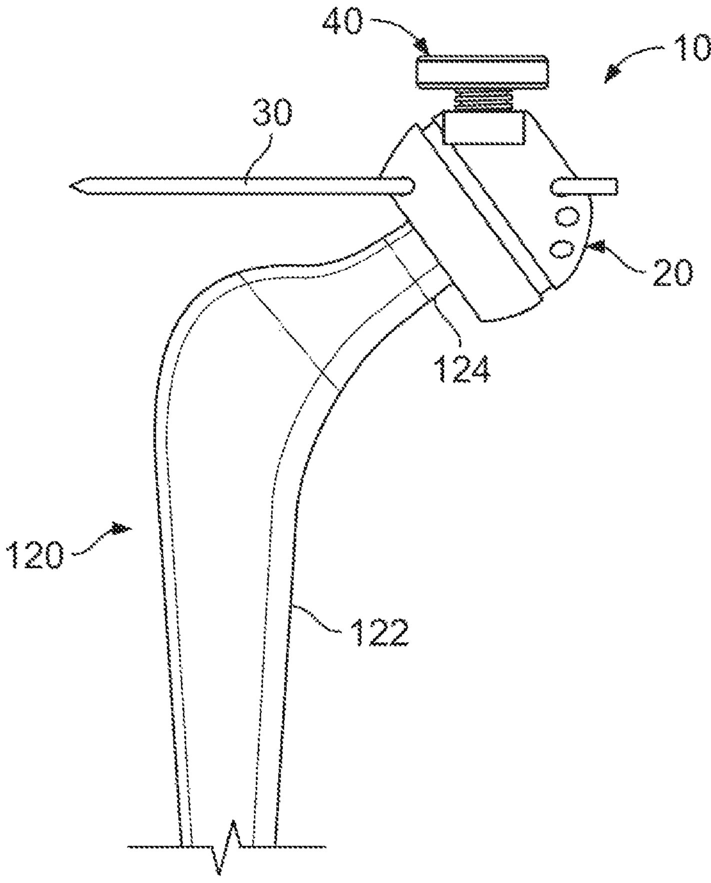
FIG. 3A front view of a femoral prosthesis according to an embodiment of the present disclosure including the alignment guide of FIG. 1A mounted thereto.

Alignment guide 10 may be provided in a system that includes a femoral prosthesis trial and a femoral prosthesis. For example, FIG. 2A depicts a femoral prosthesis trial 110, and FIG. 3A depicts a femoral prosthesis 120 that may both be included in such a system. Femoral prosthesis trial 110 includes a modular trial stem 112 and modular trial neck 114. Trial stem 112 includes broaching teeth 113 so that it serves a dual purpose of trialing and bone preparation. Trial neck 114 includes a neck 115 and a trunnion 116 extending from neck 115 so that they together define a third axis A3. Trial stem 112 defines a fourth axis A4 so that, when trial neck 114 is assembled with trial stem 112, and acute angle α is formed at the intersection of axes A3 and A4, as best shown in FIGS. 2A and 2C. Alignment guide 10 is configured to be mounted onto trunnion 116 so that first axis A1 coaligns with third axis A3, as shown in FIG. 2C. It is preferable that second axis A2 is perpendicular to fourth axis A4 in the assembly. Thus, angle θ is generally selected to be the difference between 90 degrees and angle α. For example, where angle α is 55 degrees, angle θ is 35 degrees. In this regard, the system may include a plurality of guide bodies 10 each with different θ angles, and neck trials 114 each with different a angles so that each guide body 10 has a corresponding neck trial 114. Femoral prosthesis 120 includes a stem 122 and an integrated neck 124. Femoral prosthesis 120 and femoral prosthesis trial 110 relate to each other so that axes A3, A4, and angle α are the same for each. Thus, axes A3, A4, and angle α are not depicted with respect to femoral prosthesis 120 as their depiction with respect to femoral trial 112 is sufficiently illustrative.

A method of using the aforementioned system, including alignment guide 10, to align femoral prosthesis 120 will now be described. It should be understood that the following operations do not have to be performed in the exact order described below. Instead, various steps may be handled in a different order or simultaneously. Steps may also be omitted or added unless otherwise stated therein.

In the procedure, the patient's natural femoral neck and femoral head are resected which exposes the intramedullary canal of a femur 100. The femoral canal is then prepared which may involve the use of a variety of tools such as reamers, rasps, osteotomes and/or a series of broaches of increasing size. After such tools are used to provide the initial preparation, final preparation is performed using trial stem 112. In this regard, trial stem 112 is introduced into the femoral canal by connecting a broaching handle (not shown) to trial stem 112 and using broaching handle to insert trial stem 112 along the long axis of femur 100 to a desired level based on a preoperative plan and depth indicators 111 on trial stem 112. As this occurs, cutting teeth 113 cut cancellous bone causing it to form a shape that conforms to trial stem 112 which secures trial stem 112 from inadvertent movement within femur 100.

Once the surgeon is satisfied with the positioning of trial stem 112, trial neck 114 is assembled to trial stem 112 while it remains within femur 100. Femoral head 118 is mounted onto trunnion 116 of trial neck 114, as shown in 2B. Femoral head 118 may then be inserted into a trial acetabular cup (not shown) and articulated through a range of motion to assess the artificial joint's functioning. Adjustments may be made as necessary which can include the replacement of trial neck 114 with another trial neck 114 of different length or other characteristic, such as a different a angle.

Thereafter, trial head 118 is removed, and alignment guide body 10 is mounted to trunnion 116, as shown in FIG. 2C. An indexing feature on guide body may be used to ensure that guide 10 is properly oriented on femoral neck 114. The indexing feature may be a notch etched into an exterior of guide body 20 that may be aligned with trial neck 114.

Alternatively, such as in the embodiment depicted, a flat 27 on block portion 23, which is parallel to head 42 of screw 40 and normal to an axis of threaded shaft 44, can be used as a reference so that placement of flat 27 parallel to a shoulder of stem 112 may result in alignment, for example. Alignment member 30 can also be used as an index or reference such that its orientation perpendicular to a stem axis A4 of stem 112 may result in alignment, as depicted in FIG. 2C. Alignment member 30 is then inserted into an appropriate alignment hole 26*a-b*. The surgeon will generally select the set of alignments holes 26 closest to the surgeon, and the alignment hole 26 that allows the alignment member to contact the cortical bone of the greater trochanter 102. In the example shown in FIG. 2C, alignment member 30 is inserted through the upper most alignment hole 26*a* of first set of alignment holes 26*a*. Alignment member 30 is slid through hole 26*a* until pointed tip 31 contacts the cortical bone. Locking member 40 is then advanced through first opening 24*a* and into engagement with alignment member 30 until alignment member 30 is secured from further movement. A marking 104 is then made at the target location adjacent pointed tip 31. Alignment guide 10 is removed from trial neck 114, and trial stem 112 is removed from femur 100.

Figure 3B:
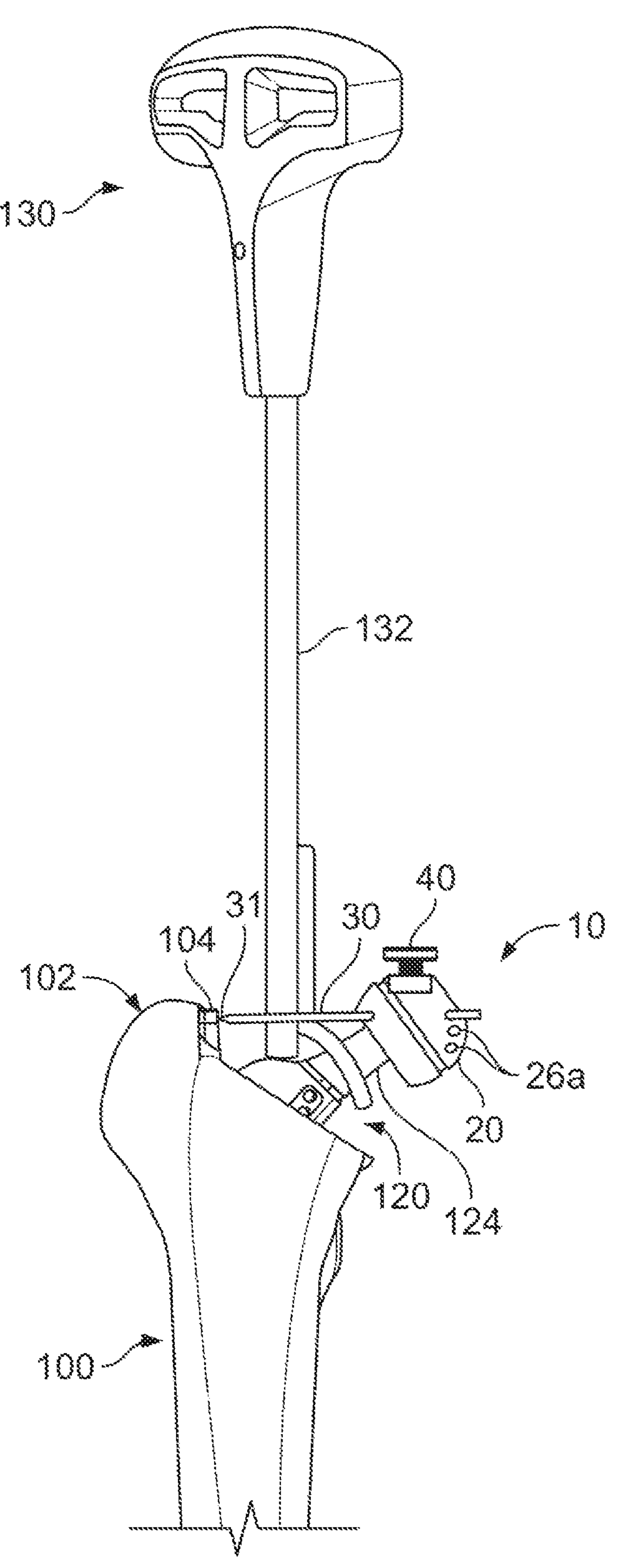
FIG. 3B illustrates implantation of the femoral prosthesis and alignment guide assembly of FIG. 3A into a femur.

Bone cement is then inserted into the femoral canal and may be pressurized to using a tamp (not shown). Alignment guide 10 is mounted to the trunnion of femoral prosthesis 120 without disturbing alignment member 30 prior to insertion into bone 100. The offset of alignment holes 26*a* by distance X relative to axis A1 provides clearance for inserter shaft 132 so that inserter shaft 132 is unimpeded by alignment member 30 and vice versa, as shown in FIG. 3B. Inserter handle 130 is then used to insert stem 122 of femoral prosthesis 120 into the bed of bone cement. It is noted that, even if femoral prosthesis 120 has depth markings on its stem to correspond to that of femoral trial 110, such markings may be obstructed by bone cement extravasating from the femoral canal. This is of no moment though as alignment guide 10 provides unobstructed visual confirmation that femoral prosthesis 120 has achieved the proper depth/height, *varus*/valgus, and version alignment.

Figure 3C:
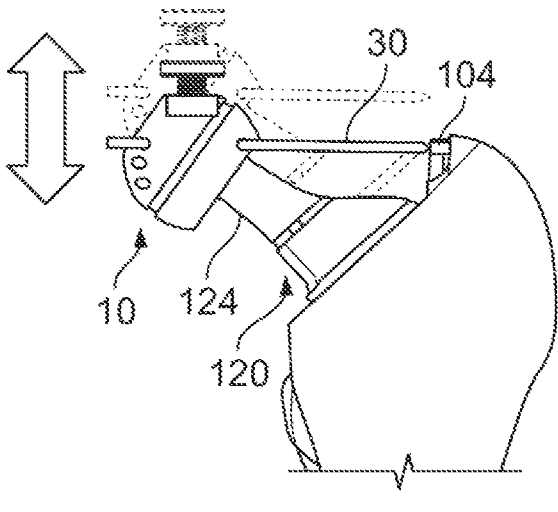
FIG. 3C illustrates aligning the depth of the femoral prosthesis and alignment guide assembly of FIG. 3A relative to the femur.
Figure 3D:
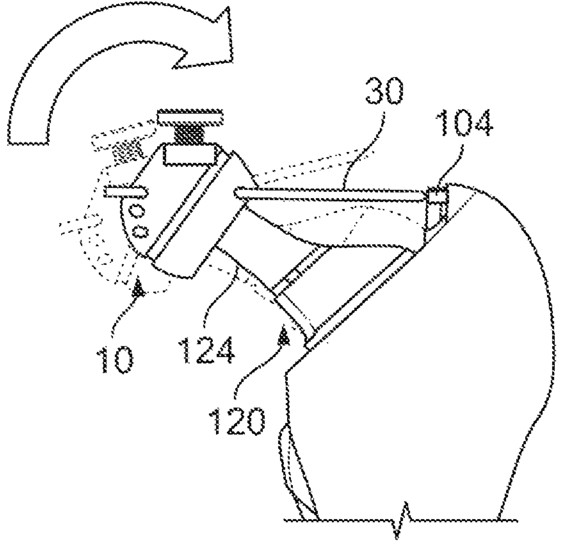
FIG. 3D illustrates aligning the femoral prosthesis and alignment guide assembly of FIG. 3A in *varus*/valgus relative to the femur.
Figure 3E:
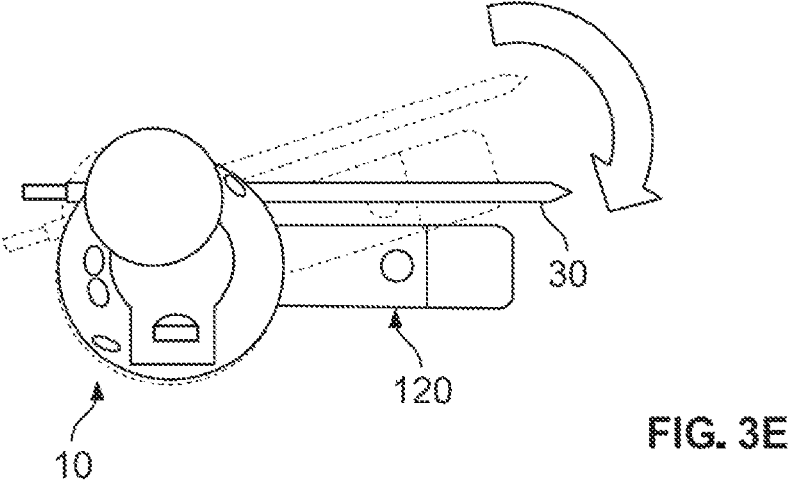
FIG. 3E illustrates aligning the femoral prosthesis and alignment guide assembly of FIG. 3A in version relative to the femur.

As shown in FIGS. 3C-3E, as femoral prosthesis 120 is advanced in the cement bed, the alignment of femoral prosthesis 120 can be determined by observing alignment member 30 relative to marking 104. In this regard, proper height/depth positioning and *varus*/valgus and version orientation is achieved when tip 31 of alignment member 30 contacts marking 104. The surgeon can therefore adjust the height/depth as shown in FIG. 3C by moving prosthesis 120 up or down, as shown in FIG. 3C, and the *varus*/valgus and version orientation by rotating femoral prosthesis 120, as shown in FIGS. 3D and 3E, respectively.

Figure 4A:
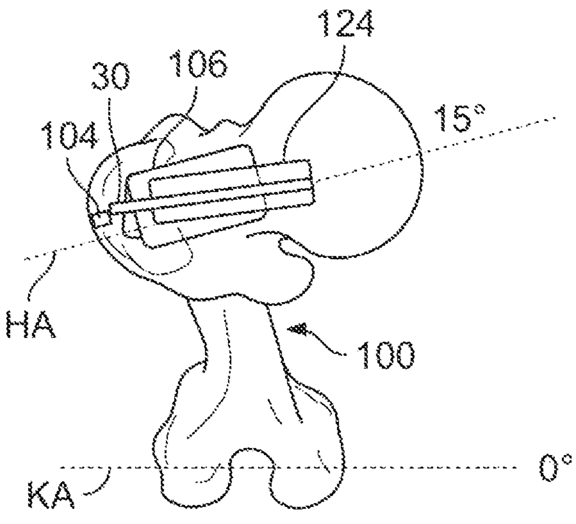
FIGS. 4A and 4B are schematics illustrating the femoral prosthesis and alignment assembly of FIG. 3A in a state of version misalignment with the femur.
Figure 4B:
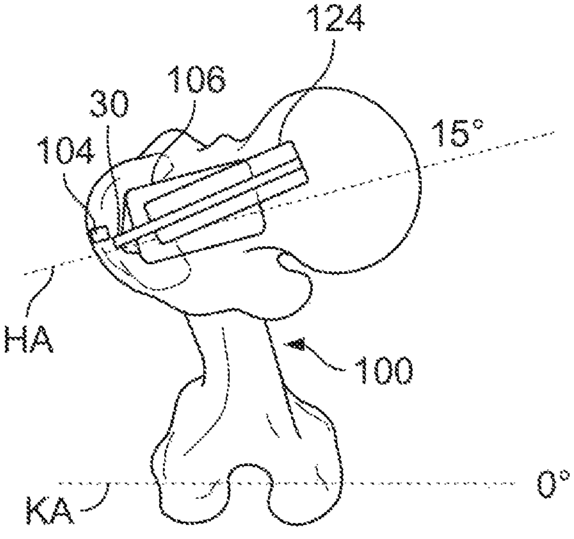
Figure 4C:
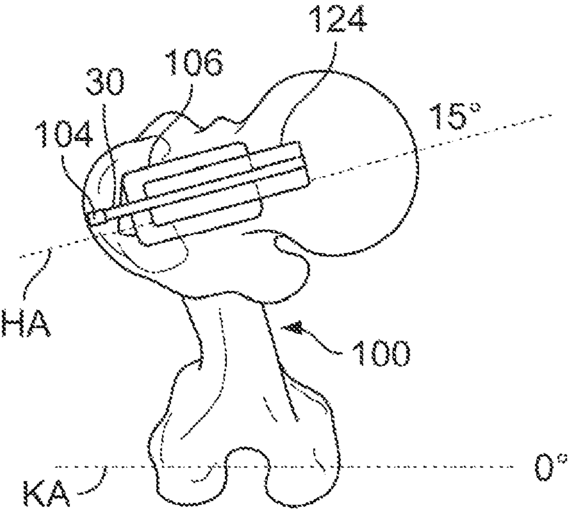
FIG. 4C is a schematic illustrating the femoral prosthesis and alignment assembly of FIG. 3A in a state of version alignment with the femur.

FIGS. 4A-4C further illustrate proper version alignment. The natural femur has a knee axis KA and a hip axis HA that is typically anteverted 15 degrees relative to the knee axis KA. However, the version angle of the natural hip may vary from patient to patient. Guide 10 is adapted to account for any version angle of a patient so as to help position the final prosthesis 120 in the same position as the former natural joint. FIGS. 4A and 4B depict misalignment of the femoral prosthesis 120 in the femoral canal 106. Thus, as shown, in each case of misalignment, alignment member 30 does not point at marking 104 which results in alignment member 30 and consequently femoral neck 114 being angled relative to the hip axis HA. However, as demonstrated in FIG. 4C, when alignment member 30 points directly at marking 104, neck 124 of femoral prosthesis 120 is positioned parallel to and aligned with the hip axis HA. Although these figures demonstrate an alignment scenario in which the orientation of member 30 in FIG. 4C results in alignment, it should be understood that guide 10 can be used by surgeon to achieve different desired orientations to satisfy different alignment conditions. For example, a surgeon may select an alignment condition in which alignment is achieved when member 30 is slightly angled relative to hip axis HA. Thus, regardless of the patient's initial anatomy, guide 10 allows the surgeon to establish any desired orientation and thereby recreate the position that was established by trial stem 112.

Once the desired alignment of height/depth, *varus*/valgus, and version is achieved, femoral prosthesis 120 is left undisturbed unto bone cement sufficiently cures, which may be a matter of minutes. Thereafter, final assembly of joint prosthesis 120 can be performed to complete the procedure.

It should be understood that the aforementioned devices and systems are merely exemplary. As such, the aforementioned principles can be achieved in alternative embodiments. For example, multiple alignment members 30 may be deployed at once to provide multiple references. Also, alignment member 30 may be a flat plate or blade instead of a headless pin. Guide body 20 can be adapted as such by providing one or more notches therein to receive the flat plate. Additionally, instead of a thumbscrew 40 for a locking member, a ball-detent mechanism or the like may be used to secure alignment member 30 in which case the ball may be located within guide body 20 and alignment member 30 may have a series of detents along its length. It is also contemplated that femoral prosthesis trial 110 may not include broaching teeth 113 such that femoral preparation is performed entirely by other accessory instruments. Thus, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthesis alignment guide, comprising:

a guide body having an opening extending at least partially therein and a first alignment hole extending entirely therethrough, the opening being configured to receive a trunnion of joint prosthesis for mounting the guide body to the joint prosthesis;

an alignment member disposed within the first alignment hole and being axially moveable therein;

a locking member engaged to the guide body and moveable from a first position in which the locking member is disengaged from the alignment member to a second position in which the locking member engages the alignment member and secures it from axial movement within the first alignment hole, wherein the opening of the guide body defines a first axis, and the first alignment hole defines a second axis, the first and second axes intersecting at an oblique angle in a projected plane.

2. The guide of claim 1, wherein the guide body has a spherical portion defining a spherical exterior surface of the guide body.

3. The guide of claim 1, wherein the first alignment hole is one of a first set of alignment holes each lying in a first plane.

4. The guide of claim 3, wherein the guide body includes a second set of alignment holes each lying in a second plane offset from the first plane.

5. The guide of claim 3, wherein the guide body includes a threaded opening extending therein an intersecting each of the first set of alignment holes, and the locking member includes a threaded shaft engaged to the threaded opening and moveable therein.

6. The guide of claim 1, wherein the locking member includes a head and a threaded shaft extending from the head, the threaded shaft threadedly engaged to the guide body.

7. The guide of claim 6, wherein the alignment member is a headless pin.

8. A prosthesis system, comprising:

a trial prosthesis having a stem and a neck;

a joint prosthesis having a stem and a neck; and a prosthesis alignment guide having a guide body, an alignment member, and a locking member, the guide body connectable to the respective necks of the trial prosthesis and joint prosthesis and having an alignment hole extending therethrough, the alignment member being slidably disposed within the alignment hole so that a first end thereof extends from the guide body, and the locking member being engaged to the guide body and moveable from a first position in which the locking member is disengaged from the alignment member and a second position in which the locking member engages the alignment member and secures it from slidable movement within the alignment hole, wherein when either the trial prosthesis or the joint prosthesis is implanted in a bone and the guide body is connected to a respective neck, the alignment member disposed through the alignment hole defines an axis that intersects a marking on the bone.

9. The guide of claim 8, wherein the stem of the trial prosthesis includes a plurality of broaching teeth.

10. The guide of claim 9, wherein the neck of the trial prosthesis is a modular neck connectable to the stem.

11. The guide of claim 8, wherein the guide body includes a threaded opening extending therein and intersecting the alignment hole.

12. The guide of claim 11, wherein the locking member includes a head and a threaded shaft extending from the head, the threaded shaft configured to threadedly engage the threaded opening.

13. The guide of claim 12, wherein the alignment member is a headless pin having a pointed tip.

14. The guide of claim 13, wherein the respective necks of the trial prosthesis and joint prosthesis each have a trunnion, and the guide body includes a tapered opening configured to respectively receive the trunnions of the trial prosthesis and joint prosthesis.

15. The guide of claim 14, wherein the respective stems of the trial prosthesis and joint prosthesis each define a stem axis, and the alignment hole defines an axis perpendicular to the stem axis of each of the trial prosthesis and joint prosthesis when the guide body is mounted thereto.

16. The guide of claim 14, wherein the tapered opening defines an axis, and the axis of the alignment hole lies in a plane offset from the axis of the tapered opening.

17. The guide of claim 16, wherein the alignment hole is one of a plurality of alignment holes lying in the plane offset from the axis of the tapered opening.

18. A method for aligning a hip prosthesis relative to a femur, comprising:

inserting a prosthesis trial into a femur;

pointing to a target location with an alignment member of an alignment guide mounted to a trunnion of the prosthesis trial;

transferring the alignment guide to a trunnion of a joint prosthesis;

inserting the joint prosthesis into the femur; and adjusting the position and orientation of the joint prosthesis within the femur until the alignment member of the alignment guide points to the target location.

19. The method of claim 18, further comprising marking the femur at the target location after the pointing step, and the adjusting step includes pointing the alignment guide at the marking.

* * * * *